US00PP35467P2

(12) United States Plant Patent
Lim

(10) Patent No.: US PP35,467 P2
(45) Date of Patent: Nov. 14, 2023

(54) FLORIBUNDA SHRUB ROSE PLANT NAMED 'ALTLADYFIRST'

(50) Latin Name: *Rosa hybrida*
Varietal Denomination: ALTladyfirst

(71) Applicant: Altman Specialty Plants Inc, Vista, CA (US)

(72) Inventor: Peter Lim, Escondido, CA (US)

(73) Assignee: Altman Specialty Plants Inc, Vista, CA (US)

( * ) Notice: Subject to any disclaimer, the term of this patent is extended or adjusted under 35 U.S.C. 154(b) by 0 days.

(21) Appl. No.: 18/091,717

(22) Filed: Dec. 30, 2022

(51) Int. Cl.
*A01H 5/02* (2018.01)
*A01H 6/74* (2018.01)

(52) U.S. Cl.
USPC ..... Plt./148

(58) Field of Classification Search
USPC ..... Plt./101, 141, 148
See application file for complete search history.

*Primary Examiner* — Susan McCormick Ewoldt
(74) *Attorney, Agent, or Firm* — Cassandra Bright

(57) ABSTRACT

A new and distinct cultivar of *Rosa* plant named 'ALTladyfirst' is disclosed, characterized by early blooming double flowers composed of pink petals with a white base. Flowers have a strong tea rose fragrance. Plants are vigorous and can be grown on their own roots. Plants are compact, flower continuously and exhibit good resistance to blackspot diseases. The new variety is a *Rosa*, normally produced as an outdoor garden or container plant.

1 Drawing Sheet

Latin name of the genus and species: *Rosa hybrida.*
Variety denomination: 'ALTladyfirst'.

BACKGROUND OF THE INVENTION

The new *Rosa* cultivar is a product of a planned breeding program conducted by the inventor, Peter Ping Lim. The objective of the breeding program was to produce vigorous new garden rose varieties with continuous blooming for ornamental commercial applications. The cross resulting in this new variety was made during June of 2012.

The seed parent is the variety *Rosa* 'WEKvossutono', U.S. Plant Pat. No. 18,473. The pollen parent is an unnamed, unpatented variety *Rosa* seedling. The new variety was selected in June of 2013 by the inventor in a group of seedlings resulting from the 2012 crossing, in a nursery in Vista, Calif.

Asexual reproduction of the new cultivar has been performed by vegetative cuttings. This was first performed at a research greenhouse in Vista, Calif. in July of 2013 and has shown that the unique features of this cultivar are stable and reproduced true to type in more than 5 successive generations.

SUMMARY OF THE INVENTION

The cultivar 'ALTladyfirst' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTladyfirst' These characteristics in combination distinguish 'ALTladyfirst' as a new and distinct *Rosa* cultivar:

1. Double flowers composed of pink petals with a white basal blotch.

2. Strong tea rose scent.
3. Light green glossy foliage resistant to black spot and powdery mildew disease.
4. Early blooming.
5. Compact plant.
6. Continuous flowering.
7. Plants can be grown on their own roots; grafting is not required.

PARENT COMPARISONS

Plants of the new cultivar 'ALTladyfirst' are similar to plants of the seed parent, in most horticultural characteristics, however, plants of the new cultivar 'ALTladyfirst' differ in the following:

1. Petal color of the new variety is pink with a white base. Petal color of the seed parent is yellow.
2. Flowers of the new variety are larger with more petals than flowers of the seed parent.

Plants of the new cultivar 'ALTladyfirst' are similar to plants of the pollen parent in most horticultural characteristics, however, plants of the new cultivar 'ALTladyfirst' differs in the following:

1. Flowers of the new variety are darker pink than flowers of the pollen parent.
2. The new variety has a weaker flower fragrance than the pollen parent.
3. Plants of the new variety are more compact than plants of the pollen parent.

COMMERCIAL COMPARISONS

Plants of the new cultivar 'ALTladyfirst' can be compared to the commercial variety *Rosa* 'Meidomonac', U.S. Plant Pat. No. 5,105. These varieties are similar in most horticultural characteristics, however 'ALTladyfirst' differs in the following:

1. Flowers of the new variety have more petals than flowers of this comparator. The new variety has on average 50 to 65 petals per flower; this comparator has on average 26 to 40 petals per flower.
2. Flowers of the new variety have a strong tea rose fragrance, while flowers of this comparator have no noticeable fragrance.
3. Petal color of the new variety is pink with a white base, while petal color of this comparator is fully pink.
4. Plants of the new variety are more compact than plants of this comparator.

Plants of the new cultivar 'ALTladyfirst' can also be compared to the commercial variety *Rosa* 'WEKblunez', U.S. Plant Pat. No. 16,572. These varieties are similar in most horticultural characteristics, however 'ALTladyfirst' differs in the following:

1. The new variety produces flowers with 50 to 65 fully formed petals. This comparator produces flowers with 28 to 52 petals and 5 to 22 petaloids.
2. Petal color of the new variety is pink with a white base, while flower color of this comparator is lilac pink.
3. Plants of the new variety are smaller than plants of this comparator.

BRIEF DESCRIPTION OF THE PHOTOGRAPH

The accompanying photograph illustrates in full color a close up of an individual flower. The photograph was taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2007 except where general terms of ordinary dictionary significance are used. The following observations and measurements describe 'ALTladyfirst' plants grown outdoors, in Palm Desert, Calif. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'ALTladyfirst'.

Market classification: Floribunda shrub rose.

PROPAGATION

Time to initiate roots: About 15 days at approximately 20° C.

Time to produce a rooted cutting: About 35 days at approximately 20° C.

PLANT

Age of plant described: Approximately 1.5 years.

Growth habit: Compact.

Container size: 2 gallon.

Height: 42 cm.

Plant spread: 65 cm.

Rootstock: Own root.

Growth rate: Moderate.

Branching characteristics: Sympodial branching.

Length of primary lateral branches: Average range 10 to 35 cm.

Diameter of lateral branches: Approximately 4 mm to 6 mm.

Quantity branches: 6 to 8 main branches, moderate lateral branches, 6 to 8 lateral branches per main branch.

Branches-Young Wood:

*Diameter.*—Approximately 4 mm.

*Texture.*—Glabrous, infrequently very soft, thorns present.

*Approximately density/quantity of prickles.*—Very sparse.

*Color.*—Near RHS Green 143C.

Branches-Old Wood:

*Diameter.*—Approximately 1 to 2 cm.

*Color.*—Near Greyed-Green 191A. Oldest section has longitudinal scales colored near Grey 201B.

*Texture.*—Glabrous. Oldest, basal growth scaly.

*Thorns.*—

*Approximately density/quantity of thorns.*—Young growth: Very sparse, soft thorns which disappear with maturity. Approximately 4 mm in diameter and 3 to 4 mm long. Colored near RHS Yellow-Green 146C. Mature growth: Sparse, apiculate thorns about 4 mm at base, 3 to 4 mm long. Colored near RHS Grey-Orange 166B. Moderately hooked.

FOLIAGE

Leaf:

*Arrangement.*—Alternate and compound.

*Quantity.*—Average 6 to 10 per main branch.

*Internode.*—Average range 3 cm to 7 cm.

*Average length.*—Approximately 10 cm.

*Average width.*—Approximately 9 cm.

Rachis:

*Average length.*—Approximately 3 to 4.5 cm.

*Average diameter.*—Approximately 2 mm.

*Color.*—Upper surface: Near RHS Yellow-Green 144C, very slightly flushed with anthocyanin near Red-Purple 61C. Lower surface: Near RHS Yellow-Green 144B.

*Texture.*—Glabrous all surfaces.

Leaflet:

*Quantity.*—5 per leaf.

*Average length.*—Approximately 5.5 cm.

*Average width.*—Approximately 3.5 cm.

*Shape of blade.*—Broad ovate.

*Apex.*—Acute.

*Base.*—Broadly rounded.

*Margin.*—Finely serrate.

*Appearance of top surface.*—Glossy.

*Appearance of bottom surface.*—Matte.

*Texture of top surface.*—Glabrous.

*Texture of bottom surface.*—Glabrous.

*Color.*—Young foliage upper side: Near RHS Green 137B. Young foliage under side: Near RHS Green 138B, very slightly flushed with anthocyanin near Red-Purple 61C. Mature foliage upper side: Near RHS Green 137A. Infrequent small spots near Red-Purple 59A. Mature foliage under side: Near RHS Green 138B.

*Venation.*—Type: Reticulate. Venation color upper side: Near RHS Yellow-Green 144C. Venation color under side: Near RHS Yellow-Green 144B.

Petiole:
*Average length.*—Approximately 2 to 3 cm.
*Average diameter.*—Approximately 3 mm.
*Color.*—Upper surface: Near RHS Yellow-Green 144C. Lower surface: Near RHS Yellow-Green 144B.
*Petiole wing.*—Typically 11 to 15 mm long and 5 mm wide. Apex apiculate. Upper surface colored near RHS Yellow-Green 144C, lower surface colored near Yellow-Green 145B.
*Texture.*—Glabrous.

FLOWER

Natural flowering season: Spring until Autumn.
Inflorescence type and habit: Singly occurring fully double rotate flowers.
Rate of flower opening: Approximately 7 days from bud to fully opened flower.
Flower longevity on plant: About one week.
Quantity of flowers: 8 to 15 fully opened flowers and buds.
Flower size:
*Diameter.*—Approximately 8 cm.
*Height.*—Approximately 4.5 cm.
Peduncle:
*Length.*—5 cm.
*Diameter.*—4 mm.
*Color.*—Near RHS Yellow-Green 144A.
*Texture.*—Softly prickly.
Petals:
*Petal arrangement.*—Multiple rotate, overlapping whorls.
*Petal quantity.*—Average 50 to 65.
*Length.*—3.5 cm.
*Width.*—4 cm.
*Shape.*—Obovate.
*Margin.*—Entire.
*Apex.*—Cordate single short notch at apex.
*Base.*—Very broad attenuate.
*Texture.*—Glabrous all surfaces.
*Color.*—When opening: Upper surface: Near RHS Red-Purple N66A flushed N66B. Large basal blotch near White N155C with basal eye near Yellow 6C. Lower surface: Near RHS Red-Purple N66A flushed N66B. Large basal blotch near White N155C with basal eye near Yellow 6D and a central, basal eye near Red-Purple 67A. Fully opened. Upper surface: Near RHS Red-Purple 62A flushed N66B. Large basal blotch near White N155C with basal eye near Yellow 6C. Lower surface: Near RHS Red-Purple 35B flushed N66B and N66D. Large basal blotch near White N155C with basal eye near Yellow 6D and a central, basal eye near Red-Purple 67B.
Bud:
*Shape.*—Ovate.
*Length.*—Approximately 3 cm.
*Diameter.*—Approximately 1.8 cm.
*Color.*—Near RHS Red-Purple N66C.
Sepals:
*Quantity.*—5.
*Length.*—2.5 cm.
*Width.*—7 mm.
*Shape.*—Narrow deltoid.
*Apex.*—Apiculate.
*Margin.*—Entire.
*Texture.*—Slightly pubescent upper surface, glabrous lower surface.
*Color.*—Interior Surface: Near RHS Greyed-Green 191B, flushed 191A. Exterior Surface: Near RHS Green 138A.
Receptacle:
*Length.*—5 mm.
*Width.*—12 mm.
*Shape.*—Flat.
*Color.*—Near RHS Green 150D.
Fragrance: Very strong tea rose scent.

REPRODUCTIVE ORGANS

Stamens:
*Quantity.*—About 20.
*Filament length.*—Approximately 4 to 7 mm.
*Filament color.*—Near RHS Yellow 2C.
Anthers:
*Length.*—3 mm.
*Shape.*—Oblate.
*Color.*—Near RHS Greyed-Orange 166B.
*Pollen.*—None observed.
Pistil: Not observed.

OTHER CHARACTERISTICS

Seeds and fruits: Not observed.
Disease/pest resistance: Good overall disease resistance to normal pests and diseases typical of garden roses. Very good resistance to blackspot diseases.

What is claimed is:

1. A new and distinct cultivar of *Rosa* plant named 'ALTladyfirst' as herein illustrated and described.

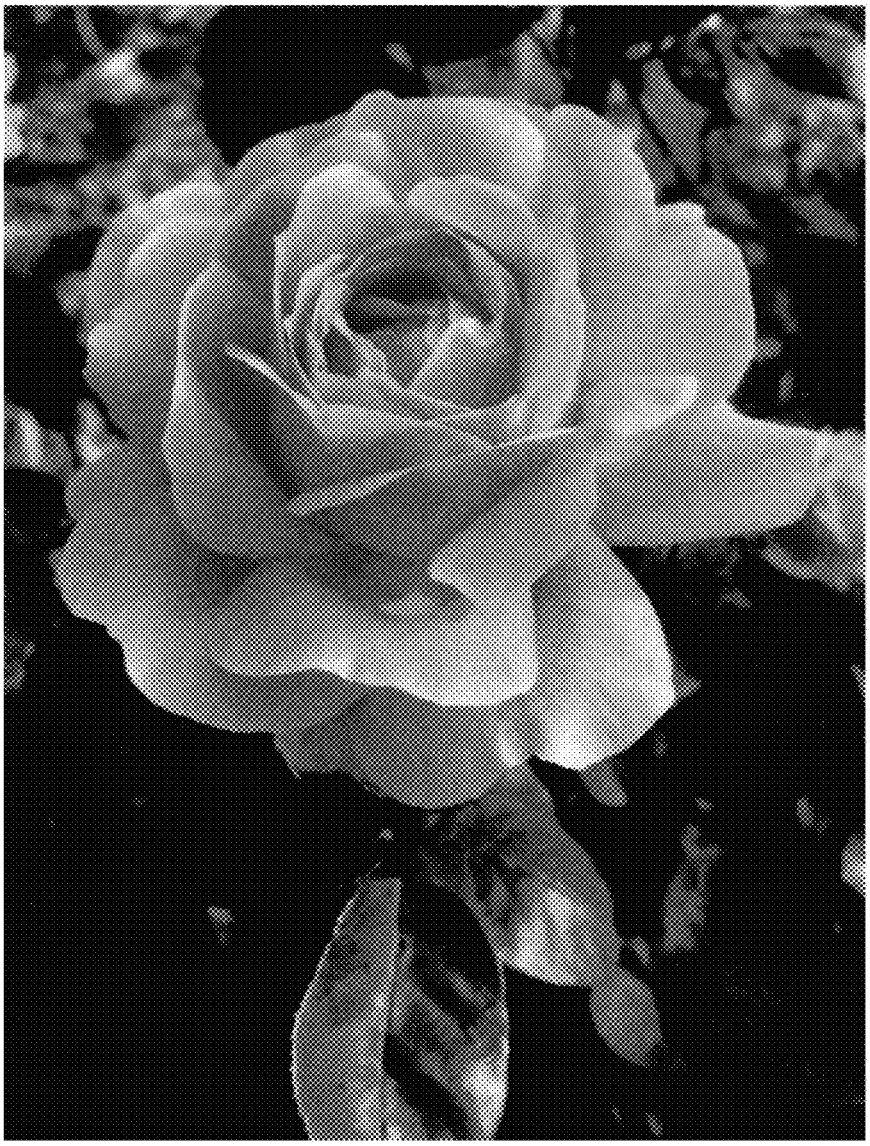

* * * * *